US00PP20488P2

(12) United States Plant Patent
Caster et al.

(10) Patent No.: US PP20,488 P2
(45) Date of Patent: Nov. 17, 2009

(54) BLUEBERRY PLANT NAMED 'DRISBLUETWO'

(50) Latin Name: *Vaccinium corymbosum*
Varietal Denomination: DrisBlueTwo

(75) Inventors: Brian Caster, Watsonville, CA (US); Arlen Draper, Payson, AZ (US)

(73) Assignee: Driscoll Strawberry Associates, Inc, Watsonville, CA (US)

( * ) Notice: Subject to any disclaimer, the term of this patent is extended or adjusted under 35 U.S.C. 154(b) by 0 days.

(21) Appl. No.: 12/151,576

(22) Filed: May 7, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Jondle & Associates, P.C.

(57) ABSTRACT

This invention relates to a new and distinct cultivar of blueberry plant named 'DrisBlueTwo' primarily characterized by medium-large berries with medium sweetness, medium acidity, and a nearly spherical berry shape and berries that have green flesh, is disclosed.

2 Drawing Sheets

Genus and species: *Vaccinium corymbosum.*
Variety denomination: 'DrisBlueTwo'.

BACKGROUND OF THE NEW PLANT

The present invention relates to a new and distinct blueberry cultivar designated 'DrisBlueTwo' and botanically known as *Vaccinium corymbosum*. This new blueberry cultivar was discovered in Watsonville in Santa Cruz County, Calif. in September 2000 and originated from a cross between the female parent blueberry plant 'Magnolia' (unpatented) and the proprietary male parent blueberry plant 'MS189' (unpatented).

The original seedling of the new cultivar was asexually propagated at a nursery in Watsonville in Monterey County, Calif. 'DrisBlueTwo' was subsequently asexually propagated and underwent further testing at a nursery in Watsonville in Santa Cruz County, Calif. for seven years. 'DrisBlueTwo' has been asexually propagated via softwood cuttings. The present invention has been found to be stable and reproduce true to type through successive asexual propagations.

SUMMARY OF THE INVENTION

The following are the most outstanding and distinguishing characteristics of this new cultivar when grown under normal horticultural practices in Watsonville in Santa Cruz, Calif.

1. Medium-large berries with medium sweetness;
2. Medium acidity and a nearly spherical berry shape; and
3. Berries that have green flesh.

DESCRIPTION OF THE PHOTOGRAPHS

The accompanying color photographs show typical specimens of the new cultivar at various stages of development as nearly true as it is possible to make in color reproductions. The photos are of plants that are seven years old.

DESCRIPTION OF THE NEW CULTIVAR

Figure 1:
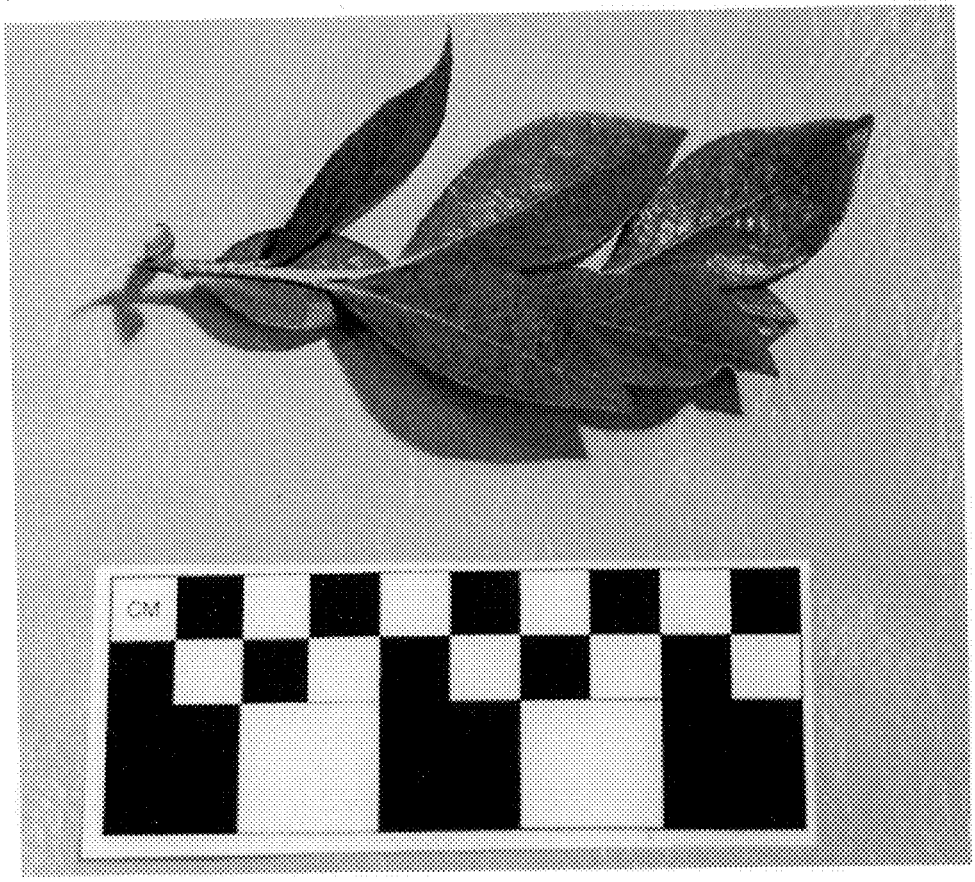
FIG. 1 shows a close-up of a leaf cluster.
Figure 2:
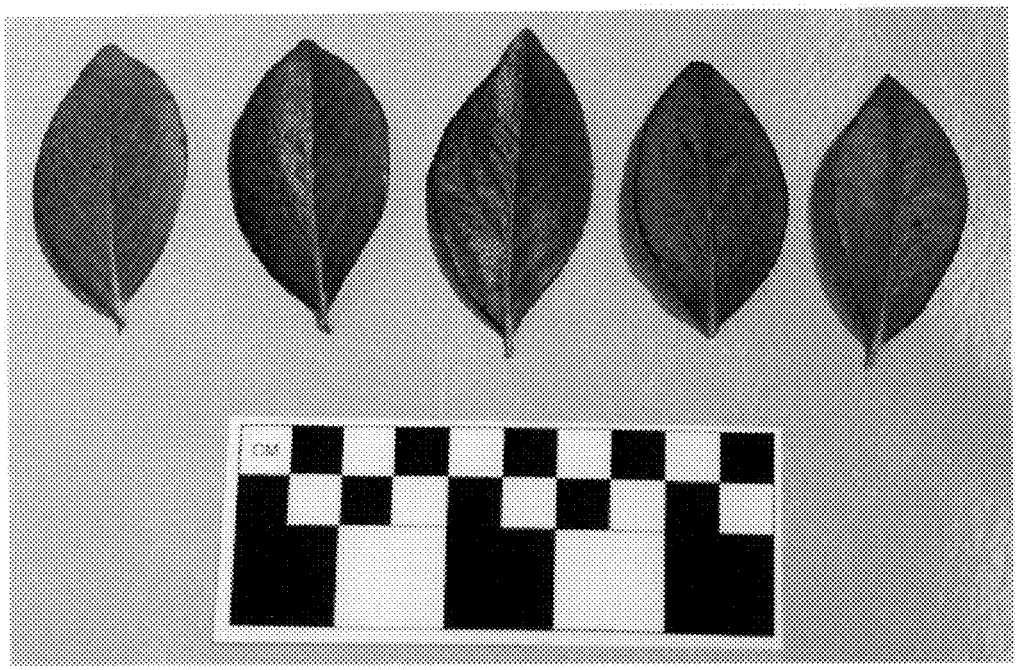
FIG. 2 shows a close-up of both the upper surface and lower surface of the leaves.
Figure 3:
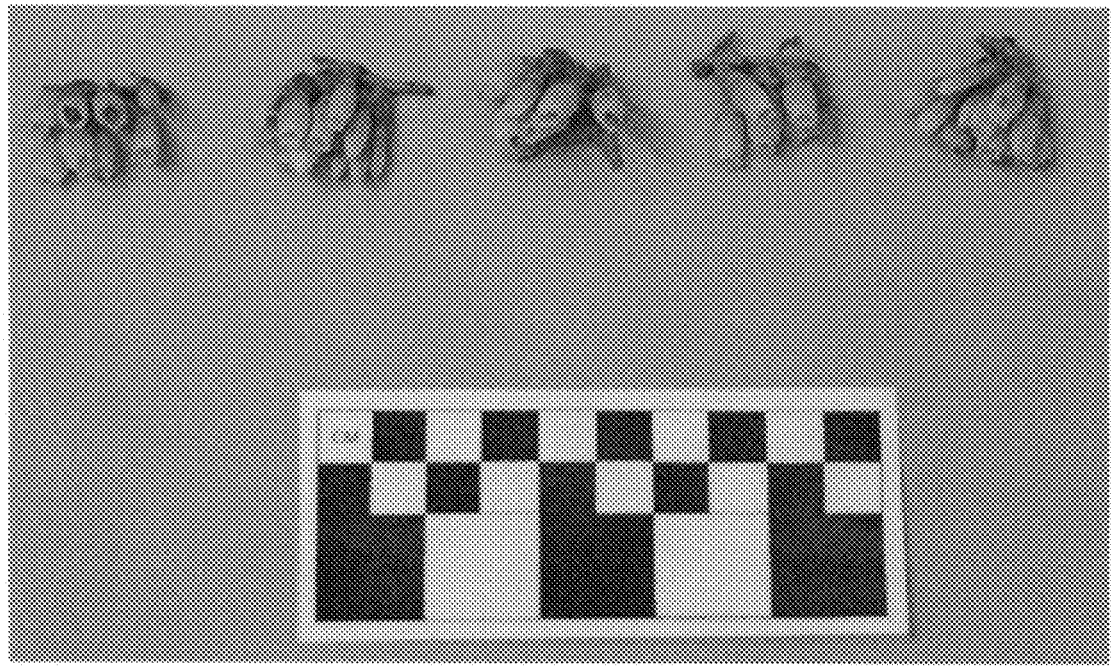
FIG. 3 shows a close-up of the mature flowers.
Figure 4:
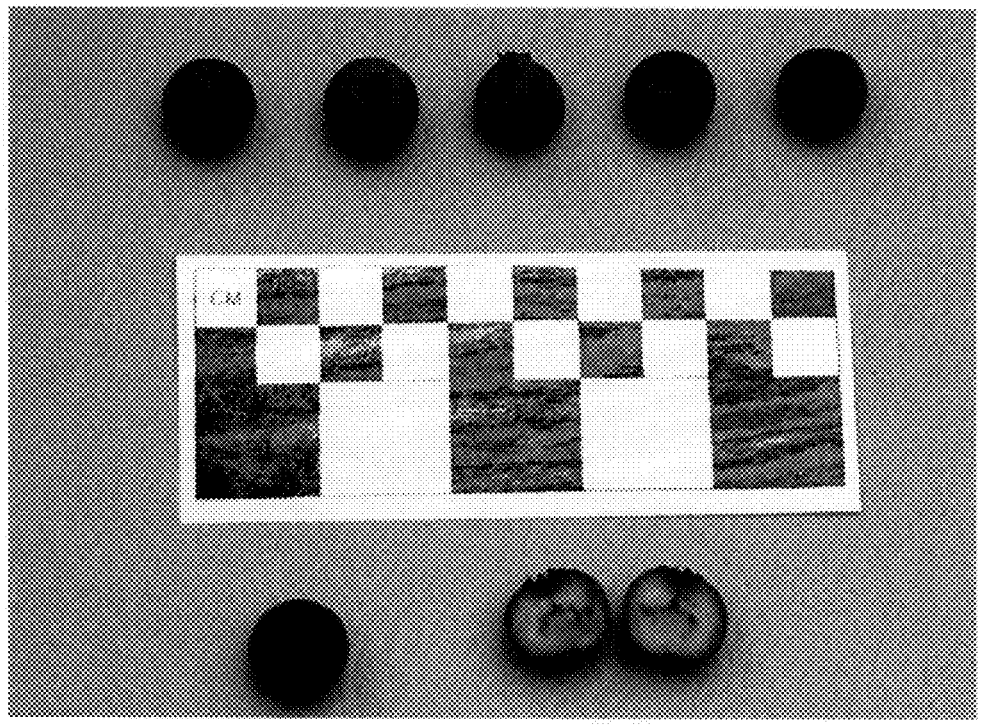
FIG. 4 shows a close-up of the whole fruit and a cross-section of the fruit.

The following description of 'DrisBlueTwo' is based on observations taken from the 2007 growing season in Santa Cruz, Calif., where the age of the 'DrisBlueTwo' plants was 7 years, while the age of the O'Neal plants were 12 years old. All descriptions are in accordance with UPOV terminology. Color designations, color descriptions, and other phenotypical descriptions may deviate from the stated values and descriptions depending upon variation in environmental, seasonal, climatic and cultural conditions. 'DrisBlueTwo' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of blueberry plant 'O'Neal' (unpatented). Table 1 includes plant, canopy and cane characteristics.

TABLE 1

| Characteristic | 'DrisBlueTwo' | 'O'Neal' |
|---|---|---|
| Plant: | | |
| Vigor | Strong | Low |
| Growth habit | Spreading to ascending shrub | Bushy |
| Chilling requirement | Medium; believed to be no more than 500-600 hours below 45° C. based on observations in Watsonville, California | Medium |
| Hardiness | At least to USDA Zone 9b based on performance in | |

TABLE 1-continued

| Characteristic | 'DrisBlueTwo' | 'O'Neal' |
|---|---|---|
| | Watsonville, California | |
| Propagation | From softwood cuttings | From softwood cuttings |
| Canopy: | | |
| Bush height (cm) | 129 | 134 |
| Canopy width (cm) | 133 | 124 |
| Height/Width ratio | 1.0 | 1.1 |
| Canes: | | |
| Mature cane diameter (cm) | 0.836 | 0.734 |
| Mature cane length (cm) | 78.2 | 69.0 |
| Mature cane color | RHS 146C (yellow-green) | RHS 138A (green) |
| Cane renewal | Medium | Weak |

Table 2 shows plant characteristics of the new variety compared with plant characteristics of blueberry plant 'O'Neal' (unpatented). Table 2 includes bud, calyx, corolla, flower and pedicel characteristics.

TABLE 2

| Characteristic | 'DrisBlueTwo' | 'O'Neal' |
|---|---|---|
| Bud: | | |
| Time of bud break | Medium | Early |
| Flowers per bud | 8 | 6 |
| Calyx: | | |
| Diameter at anthesis (cm) | 0.66 | 0.658 |
| Lobe count | 5 | 5 |
| Color | RHS 138B (medium green) | RHS 145C (light yellow-green) |
| Corolla: | | |
| Petals, general | Fused into a corolla with 5 lobes | Fused into a corolla with 5 lobes |
| Length (cm) | 1.042 | 1.014 |
| Diameter (cm) | 0.624 | 0.886 |
| Aperature diameter (cm) | 0.416 | 0.334 |
| Mature color | RHS 157B (white) | RHS 155A (white) |
| Flower: | | |
| Type | Perfect hypogynous (inferior ovary); stamens attached at base of fused corolla tube | Perfect hypogynous (inferior ovary); stamens attached at base of fused corolla tube |
| Shape | Urceolate | Urceolate |
| Number of flowers per cluster | Eight | Six |
| Fragrance | Absent to faint | Very faint |
| Size | Medium | Medium |
| 50% anthesis (full bloom) | March 15$^{th}$ | |
| 1% bloom | Medium | Early |
| Peduncle: | | |
| Length | 0.27 cm | 0.13 cm |
| Color | RHS N144D (Yellow-green) | RHS 144A (Dark yellow-green) |
| Pedicel: | | |
| Color | RHS N144D (light yellow-green) | RHS 144D (light yellow-green) |
| Length (cm) | 0.612 | 0.478 |

Table 3 shows plant characteristics of the new variety compared with plant characteristics of blueberry plant 'O'Neal' (unpatented). Table 3 includes leaf and shoot characteristics.

TABLE 3

| Characteristic | 'DrisBlueTwo' | 'O'Neal' |
|---|---|---|
| Leaves: | | |
| Arrangement | Alternate | Alternate |
| Shape | Broadly elliptic to slightly ovate | Simple and broadly elliptic to slightly ovate |
| Apex | Broadly acute to acuminate | Broadly acute |
| Base | Broadly acute | Broadly acute to slightly cuneate |
| Margin | Serrulate | Entire |
| Pubescence | Absent-glabrous | Absent-glabrous |
| Length (cm) | 0.658 | 0.662 |
| Width (cm) | 3.92 | 3.44 |
| Length/width ratio | 0.2 | 1.9 |
| Color, upper surface | RHS 137A (green) | RHS 137A (green) |
| Color, lower surface | RHS N138B (green) | RHS 138B (green) |
| Venation | Reticulate | Reticulate |
| Petiole: | | |
| Length (cm) | 0.42 | 0.40 |
| Color | RHS N144D (yellow-green) | RHS N144D (yellow-green) |
| Shoots: | | |
| Internode length (cm) | 0.862 | 1.634 |

Table 4 shows plant characteristics of the new variety compared with plant characteristics of blueberry plant 'O'Neal' (unpatented). Table 4 includes berry, skin, peduncle and seed characteristics.

TABLE 4

| Characteristic | 'DrisBlueTwo' | 'O'Neal' |
|---|---|---|
| Berry: | | |
| Shape | Nearly spherical | Slightly oblate sphere |
| Size | Medium-large | Medium |
| Weight (g) | 1.5 | 1.39 |
| Height (cm, pedicel scar to calyx) | 1.564 | 1.284 |
| Diameter (cm at widest point) | 1.796 | 1.508 |
| Height/diameter ratio | 0.87 | 0.85 |
| Firmness | Firm | Medium |
| Sweetness | Medium | Strong |
| Acidity | Medium | Mild |
| Season/timing (25% ripe) | Early to mid-season | Early season |
| Season/timing (50% ripe) | June 8$^{th}$ | June 14$^{th}$ |
| Pedicel scar diameter (cm) | 0.168 | 0.16 |
| Skin: | | |
| Bloom deposition | Weak | Medium |
| Mature color with bloom | RHS 102C (blue) | RHS 98C (violet-blue) |
| Mature color without bloom | RHS 103A (blue) | RHS 103A (blue) |
| Immature color with bloom | RHS 191A (green) | RHS 143D (light green) |
| Flesh: | | |
| Color | RHS 193C (green) | RHS 157A (green-white) |
| Seed: | | |
| Abundance | 19 per fruit | 27 per fruit |
| Color | RHS 164A (orange-brown) | RHS 165B (greyed-orange) |
| Length (cm) | 0.170 | 0.200 |
| Width (cm) | 0.130 | 0.112 |
| Length/width ratio | 1.31 | 1.79 |

Table 5 shows plant characteristics of the new variety compared with plant characteristics of blueberry plant 'O'Neal' (unpatented). Table 5 includes the reproductive organs.

TABLE 5

| Characteristic | 'DrisBlueTwo' | 'O'Neal' |
|---|---|---|
| Reproductive Organs: | | |
| Ovary color | RHS 122A (blue-green) | RHS 133C (green) |
| Pollen color | RHS 11C (yellow) | RHS 8D (light-yellow) |
| Pollen abundance | Sparse | Sparse |
| Anther length | 0.46 cm | 0.488 cm |
| Anther color | RHS N167A (greyed-orange) | RHS N170A (greyed-orange) |
| Style length, including stigma (cm) | 0.928 cm | 0.810 cm |

Resistance to diseases and insects: Disease resistance is typical of blueberry plants.

COMPARISON WITH PARENTAL VARIETIES

When 'DrisBlueTwo' is compared with the female parent 'Magnolia' (unpatented), 'DrisBlueTwo' has medium-large berries that are nearly spherical in shape, while 'Magnolia' has small berries that are oblate in shape.

When 'DrisBlueTwo' is compared to the male parent 'MS189' (unpatented), 'DrisBlueTwo' has medium-large berries with medium sweetness, while 'MS189' has medium-sized berries with mild flavor.

I claim:

1. A new and distinct cultivar of blueberry plant as described and shown herein.

* * * * *